US010849940B2

(12) United States Patent
Lundberg

(10) Patent No.: US 10,849,940 B2
(45) Date of Patent: Dec. 1, 2020

(54) PREBIOTICS OF HIGHLY REFINED CELLULOSE

(71) Applicant: Brock M. Lundberg, Osseo, WI (US)

(72) Inventor: Brock M. Lundberg, Osseo, WI (US)

(*) Notice: Subject to any disclaimer, the term of this patent is extended or adjusted under 35 U.S.C. 154(b) by 1303 days.

(21) Appl. No.: 14/684,400

(22) Filed: Jul. 2, 2015

(65) Prior Publication Data
US 2015/0290262 A1 Oct. 15, 2015

Related U.S. Application Data

(63) Continuation-in-part of application No. 13/914,181, filed on Jun. 10, 2013, now Pat. No. 10,188,131.

(51) Int. Cl.
A61K 35/747 (2015.01)
A61K 35/745 (2015.01)
A61K 35/741 (2015.01)
A61K 47/38 (2006.01)
A23L 29/269 (2016.01)
A23L 29/262 (2016.01)
A23L 33/24 (2016.01)
A23L 29/256 (2016.01)
A61K 35/00 (2006.01)

(52) U.S. Cl.
CPC .......... A61K 35/747 (2013.01); A23L 29/256 (2016.08); A23L 29/262 (2016.08); A23L 29/269 (2016.08); A23L 33/24 (2016.08); A61K 35/741 (2013.01); A61K 35/745 (2013.01); A61K 47/38 (2013.01); A61K 2035/115 (2013.01)

(58) Field of Classification Search
CPC .......... D21C 3/02; D21C 9/18; A61K 35/747; A61K 35/745; A61K 35/741; A61K 47/38; A23L 29/256; A23L 29/262; A23L 29/269
USPC ........................................................ 426/615
See application file for complete search history.

(56) References Cited

U.S. PATENT DOCUMENTS

| | | |
|---|---|---|
| 6,506,435 B1 | 1/2003 | Lundberg et al. |
| 7,094,300 B2 | 8/2006 | Harel |
| 7,094,317 B2 | 8/2006 | Lundberg et al. |
| 7,582,213 B2 | 9/2009 | Lundberg et al. |
| 8,399,040 B2 | 3/2013 | Lundberg et al. |
| 8,884,002 B2 | 11/2014 | Lundberg |
| 2006/0251789 A1* | 11/2006 | Lundberg ............... A21D 2/188 426/565 |
| 2008/0193590 A1* | 8/2008 | Lundberg ............... A21D 2/188 426/2 |
| 2009/0162322 A1* | 6/2009 | Rudolph ............... A61K 9/2009 424/93.4 |
| 2010/0189767 A1 | 7/2010 | Shimoni et al. |
| 2011/0027416 A1 | 2/2011 | Sunvold et al. |
| 2012/0172831 A1 | 7/2012 | Darcy et al. |
| 2013/0071548 A1 | 3/2013 | Williams et al. |
| 2013/0273155 A1 | 5/2013 | Yonak et al. |
| 2013/0316972 A1 | 11/2013 | Ritter et al. |

FOREIGN PATENT DOCUMENTS

EP 1072258 A1 * 1/2001 ........... A61K 9/4816

OTHER PUBLICATIONS

Lundberg et al., Enhanced crackers, chips, wafers and unleavened using highly refined cellulose fiber ingredients , U.S. Appl. No. 11/440,603, filed May 25, 2006.
Lundberg, Viscosity Control in Compositions Comprising Plant Fiber Materials , U.S. Appl. No. 12/958,118, filed Dec. 1, 2010.
Greg Aronson et al., "Reduced Fat Shortening, Roll-In, and Spreads Using Citrus Fiber Ingredients," U.S. Appl. No. 11/165,430, filed Jun. 30, 2005.
Lundberg et al., "Highly Refined Cellulosic Materials Combined With Hydrocolloids," U.S. Appl. No. 10/969,805, filed Oct. 20, 2004.
Lundberg et al., "Highly Refined Fiber Mass, Process of Their Manufacture and Products Containing the Fibers," U.S. Appl. No. 10/288,793, filed Nov. 6, 2002.
Gu, L., R Ruan, P. Chen, W. Wilcke, P. Addis. 2001. Structure Function Relationships of Highly Refined Cellulose. Transactions of the ASAE. vol. 44(6): 1707-1712).
Lundberg, Hydrocolloids Coprocessed With Cellulosic Fibers When Being Sheared Into Highly Refined Cellulose, U.S. Appl. No. 13/914,181, filed Jun. 10, 2013.

* cited by examiner

Primary Examiner — Jyoti Chawla
(74) Attorney, Agent, or Firm — Mark A. Litman & Associates, P.A.

(57) ABSTRACT

The present technology may include a stabilized mass of highly refined cellulose fiber as a prebiotic composition alone or with a probiotic composition. The prebiotic composition may comprise both the prebiotic material blended with and stabilized by highly refined cellulose fiber material. The prebiotic components may be combined with at least 1% by weight of combined probiotic as highly refined cellulose in a blend with the probiotic. The mass may flow as a liquid, may be in a frozen state or may be in a dried powder state or dried solid mass.

15 Claims, 1 Drawing Sheet

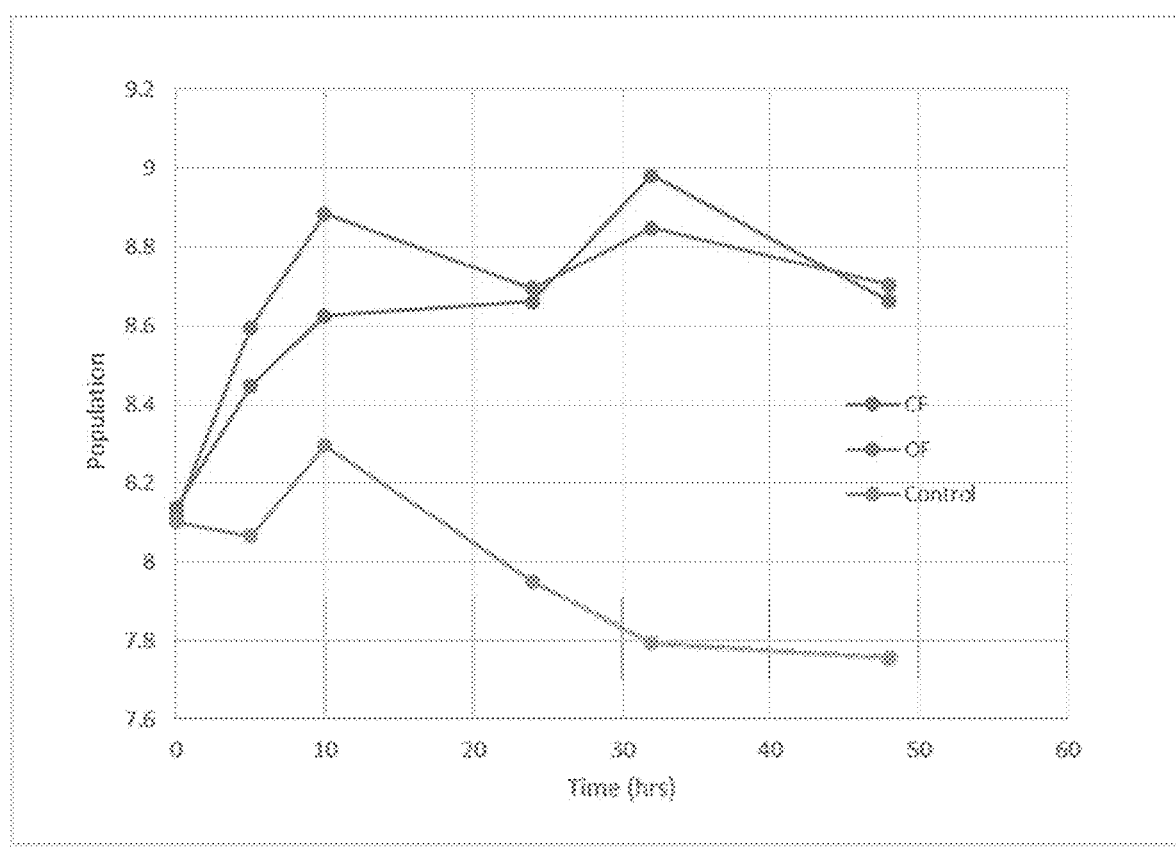

PREBIOTICS OF HIGHLY REFINED CELLULOSE

RELATED APPLICATION DATA

This application claims priority under 35 USC 120 as a Continuation-in-part from U.S. patent application Ser. No. 13/914,181, filed 10 Jun. 2013 titled "HYDROCOLLOIDS COPROCESSED WITH CELLULOSIC FIBERS WHEN BEING SHEARED INTO HIGHLY REFINED CELLULOSE" which is incorporated by reference in its entirety.

BACKGROUND OF THE INVENTION

1. Field of the Invention

The present invention relates to the field of probiotics in combination with highly refined cellulosic materials.

2. Background of the Art

Probiotics are live bacteria often found or provided in yogurt, other dairy products and pills. While probiotics have been shown to be effective in managing certain gastrointestinal conditions, they may not have the same power that prebiotics do. First, probiotics are delicate heat and stomach acid can kill them, rendering them ineffective before they have even been digested. Also, those who don't eat dairy foods for taste or dietary reasons may find ingesting adequate amounts of probiotics difficult, if not impossible.

In contrast, a Prebiotic is a specialized plant fiber that beneficially nourishes the good bacteria already in the large bowel or colon. The body itself does not digest these plant fibers. Instead, the fibers act as a fertilizer to promote the growth of many of the good bacteria in the gut. These, in turn, provide many digestive and general health benefits.

Some formulae of prebiotic supplements contain both inulin and oligofructose. This full spectrum formula treats the entire bowel wall for maximum effectiveness. And Prebiotin has been proven by numerous independent scientific studies to increase the number of healthy bacteria in the colon, the benefits of which are impressive and essential to overall health and well being.

Prehiotics and probiotics both accomplish important health tasks for the human gut, but have significant differences.

Prebiotic supplements provide a range of important benefits not just to lower gut health but to overall well-being, too. Live probiotic bacteria are easy to find and consume if dairy products are acceptable to the patient's taste and meet their dietary needs. Yogurt, for example, are known to contain probiotics. Prebiotic fibers are also easy to find if one knows where to look. Chicory Root has the highest percentage of Prebiotic Fiber per gram Prebiotic fiber is found in many fruits and vegetables, such as the skin of apples, bananas, onions and garlic, Jerusalem artichoke, chicory root and beans. Unfortunately, the minute amounts of fiber in each of these foods—such as 1 to 2 grams per serving—make ingesting enough fiber extremely difficult. Most people should consume at least 25 grams of fiber every day, and the foods that are highest in prebiotic fiber—chicory root is one such example—are nearly impossible to eat in large quantities every day. The good news is that adding a prebiotic, fiber supplement to diets is fast and simple. In supplement form, prebiotic fiber is also mild in texture and nearly tasteless, making it easy to add to water, cereal or any other food.

Over the years, medical practitioners have discovered that the colon—and specifically, the bacteria that call the colon home—is incredibly important to wellness. The healthy bacteria that live there strengthen the bowel wall, improve mineral absorption and aid in the regulation of hormone production, which has a range of essential benefits. Prebiotics fertilize these good bacteria as they stifle production of the bad, disease-causing bacteria.

Providing a strong bowel wall, improved mineral absorption and regulated hormone production is important. These have direct impact on obesity, diabetes, bone density, cancer, heart health, anxiety, a large range of lower GI problems. These conditions can improve with copious amounts of beneficial bacteria in a healthy lower gut. Prebiotics research has revealed that consuming a diet high in prebiotic fiber has a positive effect on each of these areas.

Prebiotic fiber can be a full spectrum dietary supplement that contains oligofructose and inulin. These all-natural, plant-based fibers are independently shown to nourish the beneficial bacteria in the gut. Prebiotics are more stable than probiotics and will survive the trip from mouth to lower gut intact, and it is easily added to a wide range of foods and drinks.

| PREBIOTIC VS PROBIOTIC | |
| --- | --- |
| PREBIOTICS | PROBIOTICS |
| PREBIOTICS are a special form of dietary fiber | PROBIOTICS are live bacteria in yogurt, dairy products and pills. There are hundreds of probiotic species available. Which of the hundreds of available probiotics is best is still unknown. |
| PREBIOTIC powders are not affected by heat, cold, acid or time. | PROBIOTIC bacteria must be kept alive. They may be killed by heat, stomach acid or simply die with time. |
| PREBIOTICS provide a wide range of health benefits to the otherwise healthy person. Most of these have been medically proven. | PROBIOTICS are still not clearly known to provide health benefits to the otherwise healthy. Some are suspected but still not proven. |
| PREBIOTICS nourish the good bacteria that everyone already has in their gut. | PROBIOTICS must compete with the over 1000 bacteria species already in the gut. |
| PREBIOTICS may be helpful or preventative for irritable bowel (IBS), or inflammatory bowel disease (Crohn's Disease, Ulcerative Colitis), colon polyps and cancer and those people with a leaky gut. | Certain PROBIOTIC species have been shown to be helpful for irritable bowel disease and for recurrence of certain bowel infections such as *C. difficile*. |

Prebiotics do not contain dangerous or untested chemicals, and it is suitable for vegetarian and vegan diets.

Probiotics are microorganisms that some have claimed provide health benefits when consumed. The term probiotic is currently used to name ingested microorganism associated with beneficial effects to humans and animals. Introduction of the concept is generally attributed to Nobel Prize recipient Eli Metchnikoff, who in 1907 suggested that "the dependence of the intestinal microbes on the food makes it possible to adopt measures to modify the flora in our bodies and to replace the harmful microbes by useful microbes". A significant expansion of the potential market for probiotics has led to higher requirements for scientific substantiation of putative beneficial effects conferred by the microorganisms.

The World Health Organization's 2001 definition of probiotics is "live micro-organisms which, when administered in adequate amounts, confer a health benefit on the host".[8] Following this definition, a working group convened by the FAO/WHO in May 2002 issued the "Guidelines for the Evaluation of Probiotics in Food". This first global effort was further developed in 2010, two expert groups of academic scientists and industry representatives made recommendations for the evaluation and validation of probiotic health claim. The same principles emerged from those groups as the ones expressed in the Guidelines of FAO/WHO in 2002. This definition, although widely adopted, is not acceptable to the European Food Safety Authority because it embeds a health claim which is not measurable.

A consensus definition of the term "probiotics", based on the available information and scientific evidence, was adopted after a joint Food and Agricultural Organization of the United Nations and World Health Organization expert consultation. This expert consultation defined probiotics as: "live micro-organisms which, when administered in adequate amounts, confer a health benefit on the host". The FAO/WHO consultation was also a first effort towards the assessment of probiotics. This effort is accompanied by local governmental and supra-governmental regulatory bodies requirements to better characterize health claims substantiations.

Probiotics have to be alive when administered. One of the concerns throughout the scientific literature resides in the viability and reproducibility on a large scale of the observed results, as well as the viability and stability during use and storage and finally the ability to survive in the intestinal ecosystem.

U.S. Published Patent Application 20130316972 (Ritter) provides methods and pharmaceutical compositions for treating symptoms associated with lactose intolerance and for overall improvement in gastrointestinal health. Described herein are methods and pharmaceutical compositions for improving overall gastrointestinal health or for decreasing symptoms of lactose intolerance by administering to subject in need thereof a pharmaceutical composition comprising a prebiotic, optionally in combination with effective amount of a probiotic microbe or microbes. The invention also provides diagnostic instruments and methods of diagnosing lactose intolerance using the diagnostic instruments.

U.S. Published Patent Applications 20130273155 (Yonak), 20130071548 (Williams), 20120172831 (Darcy) disclose probiotics in combination with microcrystalline cellulose, which is not highly refined cellulose.

Microcrystalline cellulose is a term for refined wood pulp and is used as a texturizer, an anticaking agent, a fat substitute, an emulsifier, an extender, and a bulking agent in food production. Microcrystalline cellulose is purified, partially depolymerized cellulose. A fine, white, odorless crystalline powder. Insoluble in water, in dilute acids, in most organic solvents, also insoluble in dilute sodium hydroxide solutions (FCC 1981).

U.S. Published Patent Application 2011027416 (Sunvold) describes a dusted pet food kibble and a process for dusting a pet food kibble comprising providing a pet food kibble in the form of a core matrix, providing a powder comprising a first component that can comprise an active ingredient, such as probiotic microorganism particles, and dusting the powder onto the pet food kibble to form a dusted kibble. The dusting can occur substantially free of a binder. An animal feed comprising a kibble in the form of a core dusted with active ingredients.

U.S. Published Patent Application 20100189767 (Shimoni) provides solid compositions of bioactive agents, in particular of probiotic microorganisms. Furthermore, the present invention provides methods for preparing these compositions. The methods include microencapsulating live microorganisms to produce a dry formulation and optionally coating the microcapsules while retaining to a significant extent the viability of the microorganisms.

Difficulty swallowing is also called dysphagia. It is usually a sign of a problem with your throat or esophagus—the muscular tube that moves food and liquids from the back of your mouth to your stomach. Although dysphagia can happen to anyone, it is most common in older adults, babies, and people who have problems of the brain or nervous system.

There are many different problems that can prevent the throat or esophagus from working properly. Some of these are minor, and others are more serious. If you have a hard time swallowing once or twice, you probably do not have a medical problem. But if you have trouble swallowing on a regular basis, you may have a more serious problem that needs treatment.

Normally, the muscles in the throat and esophagus squeeze, or contract, to move food and liquids from mouth to the stomach without problems. Sometimes, though, food and liquids have trouble getting to the stomach. There are at least two types of problems that can make it hard for food and liquids to travel down your esophagus:

The muscles and nerves that help move food through the throat and esophagus are not working right. This can happen if you have:

Had a stroke or a brain or spinal cord injury.

Certain problems with your nervous system, such as post-polio syndrome, multiple sclerosis, muscular dystrophy, or Parkinson's disease.

An immune response system problem that causes swelling (or inflammation) and weakness, such as polymyositis or dermatomyositis.

Esophogeal spasm. This means that the muscles of the esophagus suddenly squeeze. Sometimes this can prevent food from reaching the stomach.

Scleraderma. In this condition, tissues of the esophagus become hard and narrow.

Scleroderma can also make the lower esophageal muscle weak, which may cause food and stomach acid to come back up into your throat and mouth.

Something is blocking your throat or esophagus. This may happen if you have:

Gastroesophageal reflux disease (GERD). When stomach acid backs up regularly into your esophagus, it can cause ulcers in the esophagus, which can then cause scars to form. These scars can make your esophagus narrower.

Esophagitis. This is inflammation of the esophagus. This can be caused by different problems, such as GERD or having an infection or getting a pill stuck in the esophagus. It can also be caused by an allergic reaction to food or things in the air.

Diverticula. These are small sacs in the walls of the esophagus or the throat.

Esophageal tumors. These growths in the esophagus may be cancerous or not cancerous.

Masses outside the esophagus, such as lymph nodes, tumors, or bone spurs on the vertebrae that press on your esophagus.

A dry mouth can make dysphagia worse. This is because you may not have enough saliva to help move food out of your mouth and through your esophagus. A dry mouth can be caused by medicines or another health problem.

All references cited herein are incorporated by reference in their entirety.

SUMMARY OF THE INVENTION

The present technology relates to improved delivery and sustainability of prebiotic fiber, alone or in combination with probiotics before, during and after delivery of probiotics to an animal, including humans. Prebiotics are provided as highly refined cellulose (HRC) materials to provide a stable and persistent delivery system of prebiotics or as a synergistic carrier with probiotics. The use of orally ingested prebiotics as a thickened suspension or gel (alone or in combination with probiotics) as HRC materials may also be used, with or without the probiotics, to assist in moderating or treating physiological ailments such as dysphagia, using the HRC as a thickening agent in fluids, with or without probiotics being present.

A mixture of active prebiotic and probiotic agents may be stabilized and provide extended benefits within a stomach and intestinal track by at least 1%, at least 5%, at least 10%, at least 25%, at least 35%, at least 50%, at least 75% or more by weight of highly refined cellulose fiber material with respect to the combined total with probiotic agents. The prebiotic component may be dry-blended with the probiotic agents, may comprise a liquid combination (e.g., suspension or dispersion), the blend flowing as a liquid at 20° C. and 760 mm Hg atmospheric pressure and 40% relative humidity, may be a frozen mass or as a dried (pourable) powder state.

A method of stabilizing probiotic materials for oral ingestion may have steps of:
providing a solid mass of prebiotic composition comprising highly refined cellulose fibers;
if necessary combining the solid mass of prebiotic composition (a highly refined cellulose fiber material) into an ingestible composition of at least 5% by weight of the administered prebiotic composition; and
a patient ingesting the stabile prebiotic material.

The method may have the stabilized material as a dried pourable composition, a liquid composition, a solid mass or a frozen composition. The fiber composition in the method may comprise at least 0.1% by weight of highly refined cellulose, at least 2%, at least 5%, up to 98% (even 100% by total weight highly refined cellulose with respect to the total weight of administered composition or a composition comprising prebiotic and probiotic material.

A related method may moderate dysphagia by identifying a patient with dysphagia, administering a blend of highly refined cellulose and thickened liquid, the viscosity of the blend being sufficient to assist in moderating swallowing difficulties by the patient. The highly refined cellulose may be a mixture of active probiotic agents stabilized by at least 0.1% by weight of highly refined cellulose prebiotic fiber material with respect to the probiotic agents. The mixture may be mixed into existing low viscosity food and thicken the food to increase viscosity to point where swallowing with dysphagia is moderated.

BRIEF DESCRIPTION OF THE FIGURE

FIG. 1 is a graphic representation of an in vivo study in batch cultures of batch culture growth trials comparing CF (CitiFi™ additive) versus oligofructose (OF) and a control.

DETAILED DESCRIPTION OF THE INVENTION

One aspect of this technology is to show the benefits of using highly refined cellulose, and especially Citri-Fi™ fiber additives (often referred to herein as "CF") as a prebiotic, alone or in combination with probiotics products for its support and stabilizing benefits, especially as an prebiotic agent to assist with administration of probiotics in the treatment or prevention of conditions in patient. The probiotics should be present in a ration with the HRC of at least 1/100, 2/100, 5/100, 25/100, 1/2, 3/2, 25/1, 50/1 parts HRC to 1 part probiotic, up to about 1 part prebiotic HRC to 200 parts probiotic.

Probiotics must have undergone controlled evaluation to document health benefits in the target host. Only products containing live organisms shown in reproducible human studies to confer a health benefit can actually claim to be a probiotic. The correct definition of health benefit, backed with solid scientific evidence, is a strong element for the proper identification and assessment of the effect of a probiotic. This aspect represents a major challenge for scientific and industrial investigations because several difficulties arise, such as variability in the site for probiotic use (oral, vaginal, intestinal) and mode of application.

The probiotic candidate must be a taxonomically defined microbe or combination of microbes (genus, species and strain level). It is commonly admitted that most effects of probiotic are strain-specific and cannot be extended to other probiotics of the same genus or species. This calls for a precise identification of the strain, i.e. genotypic and phenotypic characterization of the tested microorganism.

Probiotics must be safe for their intended use. The 2002 FAO/WHO guidelines recommend that, though bacteria may be Generally Recognized as Safe (GRAS), the safety of the potential probiotic should be assessed by the minimum required tests:
Determination of antibiotic resistance patterns
Assessment of certain metabolic activities (e.g., D-lactate production, bile salt deconjugation)
Assessment of side-effects during human studies
Epidemiological surveillance of adverse incidents in consumers (post-market)
If the strain under evaluation belongs to a species that is a known mammalian toxin producer, it must be tested for toxin production. One possible scheme for testing toxin production has been recommended by the EU Scientific Committee on Animal Nutrition (SCAN, 2000)
If the strain under evaluation belongs to a species with known hemolytic potential, determination of hemolytic activity is required In Europe, EFSA has adopted a pre-market system for safety assessment of microbial species used in food and feed productions, in order to set priorities for the need of risk assessment. The assessment is made for a selected group of microorganisms, which if favorable, leads to the "Qualified Presumption of Safety" (QPS) status.

Finally probiotics have to be supplied in adequate amounts which may be defined as the amount able to trigger the targeted effect on the host. It depends on strain specificity, process and matrix, as well as the targeted effect. Most of reported benefits demonstrated with the traditional probiotics have been observed after ingestion of a concentration around $10^7$ to $10^8$ probiotics per gram, with serving size around 100 to 200 grams per day.

Some strains of LAB may affect pathogens by means of competitive inhibition (i.e., by competing for growth) and there is evidence to suggest that they may improve immune function by increasing the number of IgA-producing plasma cells, increasing or improving phagocytosis as well as increasing the proportion of $T.$ $lymphocytes$ and Natural Killer cells. Clinical trials have demonstrated that probiotics may decrease the incidence of respiratory tract infections and dental caries in children. LAB products might aid in the treatment of acute diarrhea, and possibly affect roptavirus infections in children and travelers' diarrhea in adults, but no products are approved for such indications.

It has been suggested that probiotics, by introducing "good" bacteria into the gut, may help maintain immune system activity, which in turn helps the body react more quickly to new infections. Antibiotics seem to reduce immune system activity as a result of killing off the normal gut bacteria.

*Helicobacter pylori*

Some strains of LAB may affect *Heliobacter pylori* infections (which may cause peptic ulcers) in adults when used in combination with standard medical treatments, but there is no standard in medical practice or regulatory approval for such treatment.

Inflammation

Some strains of LAB may modulate inflammatory and hypersensitivity responses, an observation thought to be at least in part due to the regulation of cytokine function. Clinical studies suggest that they can prevent reoccurrences of inflammatory bowel disease in adults, as well as improve milk allergies. They are not effective for treating eczema, a persistent skin inflammation. How probiotics may influence the immune system remains unclear, but a potential mechanism under research concerns the response of $T.$ $lymphocytes$ to pro-inflammatory stimuli.

Bacterial Growth Under Stress

In a study done to see the effects of stress on intestinal flora, rats that were fed probiotics had little occurrence of harmful bacteria adhering to their intestines compared to rats that were fed sterile water.

Irritable Bowel Syndrome and Colitis

In one study, a commercial strain of *Bifidobacterium infantis* improved some symptoms of irritable bowel syndrome in women. A separate small study showed that a strain of *Lactobacillus plantarum* may also be effective in reducing IBS symptoms. A study focused on *Bifidobacterium animalis* showed a reduction in discomfort and bloating in individuals with constipation-predominant IBS, as well as helping to normalize stool frequency in said individuals. For maintenance of remission of ulcerative colitis, Mutaflor (*E. coli* Nissle 1917) randomized clinical studies showed equivalence of Mutaflor and mesalazine (5-ASAs).

Necrotizing Enterocolitis (NEC)

Several clinical studies provide evidence for the potential of probiotics to lower the risk of NEC and mortality in premature infants. One meta-analysis indicated that probiotics reduce all-cause mortality and risk of having NEC by more than 50% compared with controls.

Vitamin Production

Probiotics synthesize vitamins. For example, they produce vitamin K., folic acid, and vitamin B12.

Eczema

In 2003, researchers found that a combination of L rhamnosus 19070-2 and L reuteri DSM 122460 was beneficial in the management of Atopic Dermatitis. The effect was more pronounced in patients with increased IgE levels. In 14 trials researchers found a roughly 20% reduction in the rate of atopic dermatitis (from around 34% in the children in these trials to 26%).

Bacterial Vaginosis

In 2013, researchers found that administration of hydrogen peroxide producing strains, such as *L. acidophilus* and *L. rhamnosus*, were able to normalize vaginal pH and re-balance vaginal flora, preventing and alleviating bacterial vaginosis.

| Ongoing Probiotic Research | |
|---|---|
| Strain | Claimed potential effect in humans |
| *Bacillus coagulum* GBI-30, 6086 | May improve abdominal pain and bloating in IBS patients. May increase immune response to a viral challenge. |
| *Bifidobacterium longum* subsp. *infantis* 35624 | Possible relief from abdominal pain/discomfort, bloating and constipation. |
| *Lactobacillus acidophilus* NCFM | Shown in one study to reduce the side effects of antibiotic therapy. |
| *Lactobacillus paracasei* St11 (or NCC2461) | One study indicated reduction of diarrhea in children |
| *Ilactobacillus johnsonii* La1 (=*Lactobacillus* LC1, *Lactobacillus johnsonii* NCC533) | May reduce incidence of *H. pylori*-caused gastritis and may reduce inflammation |
| *Lactobacillus plantarum* 299v | May affect symptoms of IBS. |
| *Lactobacillus reuteri* ATCC 55730 (*Lactobacillus reuteri* SD2112) | Evidence for diarrhea mitigation in children, decreased crying in infantile colic, *H. pylori* infection, antibiotic-associated side-effects, fever and diarrhea in children and number of sick days in adults. |

-continued

Ongoing Probiotic Research

| Strain | Claimed potential effect in humans |
| --- | --- |
| *Lactobacillus reuteri* Protectis (DSM 17938, daughter strain of ATCC 55730) | Evidence for shortened duration of diarrhea in children, decreased crying in infantile colic, reduced risk of diarrhea in children, may affect constipation and functional abdominal pain in children. |
| *Lactobacillus reuteri* Prodentis (DSM 17938/ATCC 55730 and ATCC PTA 5289 in combination) for oral health | Evidence for effect on gingivitis and periodontitis, preliminary evidence for reduction of oral malodor, evidence for reduction of risk factors for caries |
| *Saccharomyces boulardii* | Evidence for inhibition of antibiotic-associated diarrhea and acute diarrhea. |
| tested as mixture: *Lactobacillus rhamnosus* GR-1 ® & *Lactobacillus reuteri* RC-14 ® | In one study, oral ingestion resulted in vaginal colonisation and reduced vaginitis. May affect digestive health. |
| tested as mixture: *Lactobacillus acidophilus* CL1285 & *Lactobacillus casei* LBC80R | In vitro inhibition of *Listeria monocytogenes* and *L. innocua*, *Escherichia coli*, *Staphylococcus aureus*, *Enterococcus faecalis* and *Enterococcus faecium*. May reduce symptoms of lactose intolerance and immune stimulation. |
| *Lactobacillus plantarum* HEAL 9 & *Lactobacillus paracasei* 8700:2 | Under study for common cold infections |

Some additional forms of lactic acid bacteria include:
*Lactobacillus bulgaricus_Streptococcus thermophilus*
"*Lactobacillus bifidus*"—became new genus *Bifidobacterium*

Probiotic products contain bacteria and; or yeasts that assist in restoring the balance in our gut, Up until the 1960s, the gut microflora that they were able to identify were clostridia, lactobacilli, enterococci, and *Escherichia coli*. Since then, innovative techniques have discovered many more bacteria.

There are several different kinds of probiotics, and their health benefits are determined by the job that they do in your gut. Probiotics must be identified by their genus, species, and strain level. Here is a list of probiotics and their possible health benefits.

1. Lactobacillus

There are more than 50 species of lactobacilli. They are naturally found in the digestive, urinary, and genital systems. Foods that are fermented, like yogurt, and dietary supplements also contain these bacteria, *Lactobacillus* has been used for treating and preventing a wide variety of diseases and conditions.

Some of the lactobacilli found in foods and supplements are *Lactobacillus acidophilus*, *L. acidophihis* DDS-1, *Lactobacillus blugaricus*, *Lactobacillus rhamnosus* GG, *Lactobacillus plantarium*, *Lactobacillus reuteri*, *Lactobacillus salivarius*, *Lactobacillus casei*, *Lactobacillus johnsonii* and *Lactobacillus gassers*.

More research is needed regarding probiotics and their potential health benefits before any definitive claims can be made about their effects. However, studies have shown some benefits linked to *Lactobacillus* and treating and/or preventing yeast infections, urinary tract infection, irritable bowel syndrome, antibiotic-related diarrhea, traveler's diarrhea, diarrhea resulting from *Clostridium difficile*, treating lactose intolerance, skin disorders (fever blisters, eczema, acne, and canker sores), and prevention of respiratory infections. More specifically, results from some of the studies are as follows:

*Lactobacillus* GG was given to children 5 to 14 years of age with irritable bowel syndrome over eight weeks' time. They were given 3 billion cells twice per day. This reduced the frequency and severity of abdominal pain,

*Lactobacillus* GG was given to children taking antibiotics and there was a decrease in reported diarrhea,

*Lactobacillus casei*, *Lactobacillus bulgarios*, and *Streptococcus thermophilus* given twice daily during antibiotic treatment and for a week later decreased the risk of diarrhea in hospitalized adults.

*Lactobacillus* GG-containing milk was given to children 1 to 6 years of age who attended day care. They got fewer or less severe lung infections than those who did not drink it

*Lactobacillus gasseri* and *Lactobacillus rhamnosus* vaginal capsules lengthened the time in between bacterial vaginosisinfections.

*Lactobacillus* GG reduced the risk of traveler's diarrhea by 47% in a study with 245 people who traveled to 14 worldwide geographic regions.

2. Bifidobacteria

There are approximately 30 species of bifidobacteria. The make up approximately 90% of the healthy bacteria in the colon. They appear in the intestinal tract within days of birth, especially in breastfed infants.

Some of the bifidobacteria used as probiotics are *Bifodbacterium bifidum*, *Bifodbacterium lactis*, *Bifodbacterium longum*, *Bifodbacterium breve*, *Bifodbacterium infantis*, *Bifodbacterium thermophilum*, and *Bifodbacterium pseudolongum*.

As with all probiotics, more research is needed to prove a definitive benefit, but studies have shown that bifidobacteria can help with IBS, dental cavities, improved blood lipids, and glucose tolerance.

*Bifidobacterium infantis* 35624 was given to 362 patients with irritable bowel syndrome in a four-week study. They showed improvement in the symptoms of abdominal pain, bloating, bowel dysfunction, incomplete evacuation, straining, and the passage of gas.

Salivary levels of bifidobacteria are associated with dental cavities in adults and children.

*Bifidobucterium lactis* Bb12 is reported to have beneficial effects on metabolism, including lowered serum LDLcholesterol in people with type 2 diabetes, increased HDL adult women, and improved glucose tolerance during pregnancy.

3. *Saccharomyces boulardii*

This is also known as *S. boulardii* and is the only yeast probiotic. Some studies have shown that it is effective in preventing and treating diarrhea associated with the use of antibiotics and traveler's diarrhea. It has also been reported to prevent the reoccurrence of *Clostridium difficile*, to treat acne, and to reduce side effects of treatment for *Helicobacter pylori*.

4. *Streptococcus thermophilus*

This produces large quantities of the enzyme lactase, making it effective, according to some reports, in the prevention of lactose intolerance.

5. *Enterococcus faecium*

This is normally found in the intestinal tract of humans and animals.

a. *E. faecium* SF68b. *E. faecium* M-74

6. *Leuconostoc*

This has been used extensively in food processing throughout human history, and ingestion of foods containing live bacteria, dead bacteria, and metabolites of these microorganisms has taken place for a long time.

Highly refined cellulose materials (HRC materials) are well known in the literature and are disclosed, for example, in U.S. patent application Ser. No. 11/440,603, filed May 25, 2006, which is in turn a continuation-in-part of U.S. patent application Ser. No. 11/165,430, filed Jun. 30, 2005, titled "REDUCED FAT SHORTENING, ROLL-IN, AND SPREADS USING CITRUS FIBER INGREDIENTS," which is a continuation-in-part of U.S. patent application Ser. No. 10/969,805, filed 20 Oct. 2004, and titled "HIGHLY REFINED CELLULOSIC MATERIALS COMBINED WITH HYDROCOLLOIDS," which is a continuation-in-part of U.S. patent application Ser. No. 10/288,793, filed Nov. 6, 2002, titled "HIGHLY REFINED FIBER MASS, PROCESS OF THEIR MANUFACTURE AND PRODUCTS CONTAINING THE FIBERS." The enzymatically modified highly refined cellulose fibers of U.S. patent application Ser. No. 12/958,118, filed 1 Dec. 2010 are also useful in the practice of the present technology, and that application is incorporated herein by reference in its entirety. Issued U.S. Patents of the inventor such as U.S. Pat. Nos. 8,399,040; 7,582,213; 7,094,300; and 6,506,435 are also incorporated by reference in their entirety.

According to the above cited U.S. patent application Ser. No. 13/914,181 (Lundberg), the probiotic may also be accrued within a unique proprietary thickening agent described therein. That thickening composition may be made by a process of forming a highly refined cellulose and hydrocolloid product by, in order: a) providing a wet supply of natural, unrefined organic fibers, b) introducing a hydrocolloid to the supply of natural, unrefined organic fibers to form a mixture, c) shearing the mixture to refine the natural, unrefined organic fibers into highly refined cellulose blended with the hydrocolloid; and co-drying the highly refined cellulose blended with the hydrocolloid to form a highly refined cellulose fiber product having at least 10% by total weight of insoluble fiber. The hydrocolloid may be, for example, a base of guar, xanthan, carrageenan, or carboxymethyl cellulose. The resulting product is a high parenchymal refined cellulose fiber additive product having a high parenchymal content fiber reagent that has organic fiber plant mass comprising at least 30% by weight of all fiber mass as parenchymal fiber mass and a hydrocolloid bound to the fiber during shearing of an unrefined cellulose fiber mass during formation of a highly refined cellulose mass as a high parenchymal fiber additive product having at least 10% by total weight of insoluble fiber. The product may also be described as a highly refined citrus fiber product comprising citrus fiber co-sheared and co-dried with at least 0.5% by weight hydrocolloid and comprising at least 10% by weight of insoluble citrus fiber. The high parenchymal fiber additive product may be based on a primary cell wall or parenchymal fiber product having at least 50% by weight of the fiber content of the natural, unrefined organic fibers as unbleached primary cell wall fiber or parenchymal fiber co-sheared and co-dried with at least 0.5% by weight of the parenchymal additive as hydrocolloid and the parenchymal fiber additive comprising at least 10% by weight of insoluble citrus fiber. The organic fiber mass comprises highly refined cellulose microfibers derived from organic fiber plant mass comprising at least 30% by weight of all fiber mass as parenchymal fiber mass, the highly refined cellulose product having a water retention capacity of at least about 5 g $H_2O$/g dry highly refined cellulose product, and the highly refined cellulose microfibers have a water retention capacity of at least 5 g $H_2O$/g dry highly refined cellulose product and the and the product further comprises less than 50% of the fiber and/or colored content of the fiber unbleached. The product may have the organic fiber mass of at least 50% by weight of fiber mass from organic products selected from the group consisting of sugar beets, citrus fruit, carrots, grapes, tomatoes, chicory, potatoes, pineapple, apples and cranberries and at least 80% of the organic fiber mass may be derived from fruit and root cell mass.

A highly refined cellulose thickening or carrying composition for use with the present technology product comprising microfibers derived from organic fiber plant mass formed by shearing and physically may be in a non-refined natural, organic cellulosic fiber into the highly refined cellulosic fiber in the presence of at least one hydrocolloid present in a weight ratio of at least 1:10, hydrocolloid/microfiber, the highly refined cellulose product displaying a viscosity at a 1% by weight concentration in water at 1 revolution per minute of at least 20,000 centipoise at 20° C. The organic fiber plant mass may contain material from at least 50% by weight of fiber mass from organic products selected from the first group consisting of sugar beets, citrus fruit, carrots, grapes, tomatoes, chicory, potatoes, pineapple, apples and cranberries and wherein at least 80% of the organic mass is derived from fruit and root cell mass of the first group. Another description of a method for refining cellulosic material from the fruit and 0plant materials for use in the practice of the present technology may include: soaking raw material from organic fiber plant mass comprising at least 50% by weight of all fiber mass as parenchymal fiber mass in an aqueous solution with less than 1% NaOH; draining the raw material and allowing the raw material to sit for sufficient time to enable cells in the raw material to open cells and expand the raw material into an expanded fiber product, the soaking producing soaked raw materials; and refining the soaked raw material to produce refined material by shearing the soaked raw materials in the presence of at least 10% by weight of hydrocolloid with respect to the weight of the organic fiber plant mass; and then drying the sheared mixture of highly refined cellulosic fiber and hydrocolloid.

Procedures

Example 1

To provide insight on the feasibility and mechanism by which prebiotics can function, in vitro studies in batch cultures were conducted. The batch culture growth trial compared CF versus oligofructose (OF) and a control. The cultures were inoculated with bacteria and growth measured over time. The bacteria strain that was inoculated and measured for the various treatments was *bifidobacterium*. The results are shown in the chart below.

Results showed the CF test had an faster growth curve of *bifidobacterium* compared to a control. The population growth of CF grew over the course of the test whereas the control spiked at 10 hours but then declined. Meanwhile, compared to OF, the CF test had a slightly slower growth in the beginning compared to OF but then continued to increase over time to still reach or even exceed levels of *bifidobacterium* compared to OF. OF is even a soluble polysaccharide that would have a tendency to be broken down and digested by the *bifidobacterium* compared to CF, but clearly this shows how CF creates an environment conducive to growth and thus, has prebiotic activity.

1) Liquid Mixture from Probiotic

The Citri-Fi™ fiber and dry active bacterial probiotic blend samples will be processed using batch or continuous commercial production lines. After bof ingredients, liquid blends may be packaged into 1-lbs aluminum Scholle™ bags.

For shelf life testing, the blends would be evaluated at four weeks for the standard shelf life (SSL) probiotic blend product and 12 weeks for the extended shelf life (ESL) blends. Total plate count, major pathogens including *Salmonella, Listeria monocytogenes, E. Coli* 0157H7, pH, and sensory properties (viscosity, color) will be measured when the product is first made and at the end of the typical shelf life, i.e., 4 weeks for SSL and 12 weeks for ESL.

| Ingredient | Control (%) | Test A (%) | Test B (%) |
|---|---|---|---|
| Dry active probiotic | 100 | 95 | 75 |
| Water | X | X | 18.64 |
| Citri-Fi ™ 200 FG | X | X | 1.36 |
| Sugar (granulated) | X | 5 | 5 |
| Total | 100% | 100% | 100% |

TABLE 3

Probiotic Blend Proposed Testing Results

| Ingredient | Control (%) | Test A (%) | Test B (%) | Test C (%) | Test D (%) |
|---|---|---|---|---|---|
| Dried active probiotic | X | X | 20 | 5 | 20 |
| Dried active probiotic co-processed with CF 200FG | X | 25 | X | X | X |
| active probiotic co-dried with sugar (25%) | 25 | X | X | 20 | X |
| Water | 75 | 75 | 60 | 75 | 60 |
| Add'l water | X | X | 18.64 | X | 18.64 |
| CF 100 FG | X | X | X | X | X |
| CF 200 FG | X | X | 1.36 | X | 1.36 |
| Sugar (granulated) | X | X | X | 5 | X |
| Total | 100% | 100% | 100% | 100% | 100% |
| Initial Density (g/mL) | 0.361 | 0.385 | 0.663 | 0.47 | 0.663 |
| 1 hr Density (g/mL) | 0.516 | 0.405 | 0.663 | 1.175 | 0.663 |
| Observations | Settling of foam at 30 mL | Settling of foam at 5 mL | No change | Settling of foam at 40 mL | No change |

D. Shelf Life Evaluation:

The results suggested that both the ESL and the SSL liquid Citri-Fi and dry active probiotic blends can successfully achieve the designed shelf life with minimal microbial safety challenge and quality alteration. The interactions between Citri-Fi and probiotic components during storage are minimal and resultant changes in egg safety and functionality is not significant. The property would be tested on day-1 samples in comparison with that on the 12-week for ESL and that on 4-week for SSL. The cake function for the probiotic samples both in the beginning and at the end of their shelf life would be expected to be good.

TABLE 1

Expected Comparison between samples at day-1 and at end of shelf life

| Test dates | ESL blend | | | | | | | SSL Blend | | | | | | |
|---|---|---|---|---|---|---|---|---|---|---|---|---|---|---|
| | TPC* | | Vis | Cake** | Color | | | TPC* | | Vis | Cake** | Color | | |
| | cfu/ml | pH | (cP) | function | L | a | b | cfu/ml | pH | (cP) | function | L | a | b |
| Day-1 | <10 | 6.9 | 1080 | good | 71 | 14 | 46 | <10 | 6.9 | 333 | Good | 68 | 16 | 53 |
| 4-wk | | | | | | | | <10 | 6.9 | 267 | Good | 67 | 16 | 50 |
| 12-wk | <10 | 6.8 | 1780 | good | 71 | 13 | 45 | | | | | | | |

TPC* --all samples would be tested for major pathogens including *Salmonella, Listeria, E. Coli* O157:H7 and would be found negative both at the beginning and at the end of the shelf life tested.

It is important to note the difference in the practice of the present technology of the term "highly refined cellulose" HRC product as compared to the more conventional material referred to as "dietary fiber." Many teachings of baked products including cracker products include the use of dietary fiber as one method of improving dietary or nutritional benefits in the baked good. Dietary fiber generally refers to the use of bulk fiber material, usually in its less processed state (e.g., dried but not highly sheared), so that the fiber remains substantially intact and even cell wall structure and cell morphology can be readily seen under microscopic examination (e.g., 40× to 500× examination).

Published U.S. Patent Applications Nos. 20050274469; 20050271790; 20050074542; 20040086626; and 20030116289 disclose highly refined cellulose materials.

Prior art results according to the Chen patents were WRC values were measured for both the aqueous HRC gel and dried HRC powder using a process that used NaOH concentrations ranging from about 0.004 to 0.025 g NaOH/g water. The WRC values for both the HRC gel and HRC powder were in the range of about 20 to at least about 56 g $H_2O$/g dry HRC, depending on the concentration of the alkaline solutions as measured by AACC 56-10 at varying solids content, which were typically less than 5% and most commonly at 1%. Maximum WRC values for the gel of at least about 56 g $H_2O$/g dry HRC were obtained with a NaOH concentration of about 0.007 g NaOH/g H2O. Drying the HRC gel resulted in a reduction of about three (3) to 15% in WRC, which may be attributed to structural damages such as recrystallization caused by dehydration. However, the HRC powder also exhibited high WRC values, having a maximum WRC value of at least about 56 g $H_2O$/g dry HRC at a NaOH concentration of about 0.007 g NaOH/g $H_2O$. Compared with WRC values for even earlier prior art HRC products of 3.5 to 10 g water/g dry powdered cellulose reported by Ang and Miller in Cereal Foods World, Multiple Functions of Powdered Cellulose as a Food Ingredient, Vol. 36 (7): 558-564 (1991), it was shown that both the HRC gel and powder of the Chen Patents had a much higher water-holding capacity than prior art materials known at the time of the invention.

Determination of Water-Retention Capacity (WRC) and Oil-Retention Capacity (ORC) WRC is a measure of the amount of water retained under standard centrifuge. The WRC values for both aqueous HRC gel and freeze-dried HRC were determined in accordance with Method 56-10 of the American Association of Cereal Chemists (AACC), except the water holding capacities were measured in a 1% hydrated state. In the ORC (oil retention capacity) test, the same procedure was used except oil was used instead of water.

Determination of Pore Size and Microsurface Area Both the pore size and the microsurface area of freeze-dried HRC samples were measured using a Micromeritics™ 2000 from Micromeritice Instrument Co. The test sample was weighed with a precision of 0.0001 g. In all cases, the test sample weight was more than 100 mg to reduce the effect of weighing errors. At 85° C. and 6 mmHg vacuum, the sample was degassed, and moisture and other contaminants were removed. The degassed sample was analyzed in a nitrogen gas environment. Average pore diameter, BET surface area and Langmuir surface area were measured. The BET surface area values were determined by calculating the monolayer volume of adsorbed gas from the isotherm data. The Langmuir surface area values were obtained by relating the surface area to the volume of gas adsorbed as a monolayer.

Results and Discussion—Pore Size and Surface Area

Average pore size is a measure of openness of the HRC structure. The average pore size increased rapidly as NaOH concentration was increased to 0.007%, then slowly with further increase in NaOH concentration. The surface area reached a maximum value at 0.007% NaOH, which also coincides with the maximum WRC discussed above. The decrease in surface area after the maximum value seems to suggest an increase in the ratio of large pores to small pores, which may contribute to the decrease in total surface area. In one embodiment, the processes of the Lundberg Application removes lignin to a sufficient degree or substantially inactivates it such that undesirable fiber clumping does not occur There is not a large apparent difference in terms of WHC/viscosity between the two products (the Chen product and the product of the Lundberg Application) in a wet form, but there is a significant and commercially and technically important difference between the products/processes is that 1) Chen never provided a method for drying the gel product or 2) rehydrating the dry product. Additionally, 3) the present process for citrus has no required chemical treatment and does not need any mechanical treatments to produce a dry product that rehydrates to a high WHC/viscosity gel. Additionally, there is less concern about all the surface area, and pore size measurements.

It is desired that the highly refined cellulose fiber materials used in the practice of the present technology have the following properties. The HRC materials should provide a viscosity of at least 200 cps (preferably at least 300 cps) at 20 C in a concentration of 3% in deionized water after mild stirring for 4 hours, a water retention capacity of at least 8× the dry weight of fiber (preferably at least 10×, at least 15× and at least 20×), which may also be determined by filtering saturated fiber mass, draining excess water (e.g., under mild pressure of 50 g/10 cm² for three minutes), weighing the drained wet fiber mass, then dehydrating the drained mass (to less than 5% water retention/weight of the fiber) and weighing the dried product to determine the amount of absorbed water removed. This latter method is less preferred, but can address the issue that drying of fibers often changes their physical properties, and particularly dried fibers (unless additionally sheared) often lose WRC after drying.

A highly refined cellulosic material (e.g., cellulose, modified celluloses, derivatized celluloses, hemicellulose, lignin, etc.) product can be prepared by generally moderate treatment and still provide properties that are equivalent to or improved upon the properties of the best highly refined cellulose products produced from more intense and environmentally unfriendly processes. Fruit or vegetable cells with an exclusively parenchymal cell wall structure can be treated with a generally mild process to form highly absorbent microfibers. Cells from citrus fruit and sugar beets are particularly available in large volumes to allow volume processing to generate highly refined cellulose fibers with both unique and improved properties. These exclusively parenchymal microfibers (hereinafter referred to as EPM's) have improved moisture retention and thickening properties that enable the fibers to provide unique benefits when combined into edible products (e.g., baked goods, liquefied foods, whipped foods, meats, meat fillers, dairy products, yogurt, frozen food entrees, ice cream, etc.) and in mixtures that can be used to generate edible food products (e.g., baking ingredients, dehydrated or low hydration products).

A new process for making HRC cellulose from parenchyma cell wall products, e.g. citrus fruit and sugar beets by-products, is performed in the absence of a hydroxide soaking step. This is a significant advance over the prior art as described by the Chen and Lundberg patents. Dinand, et al. (U.S. Pat. No. 5,964,983) also recommends the use of a chemical treatment step in addition to bleaching. In the present invention we are able to attain higher functionality (measured as viscosity) compared to Dinand et al. even though we use less chemical treatment, which is likely due to the higher amount of shear and chemical energy we put into the materials. The product is able to display the same or improved water retention properties and physical properties of the more strenuously refined agricultural products of the prior art, and in some cases can provide even higher water retention values, thickening and other properties that can produce unique benefits in particular fields of use.

General descriptions of the invention include a highly refined cellulose product comprising microfibers derived from organic fiber plant mass comprising at least 50% by weight of all fiber mass as parenchymal fiber mass, the highly refined cellulose product having an alkaline water retention capacity of at least about 25 g $H_2O$/g dry highly refined cellulose product and methods for providing and using these products. The highly refined cellulose product may have a water retention capacity of at least 50 g $H_2O$/g dry highly refined cellulose product.

Parenchymal cell walls refer to the soft or succulent tissue, which is the most abundant cell wall type in edible plants. For instance, in sugar beets, the parenchyma cells are the most abundant tissue the surrounds the secondary vascular tissues (xylem and phloem). Parenchymal cell walls contain relatively thin cell walls compared to secondary cell walls are tied together by pectin (Haard and Chism, 1996, Food Chemistry. Ed. By Fennema. Marcel Dekker NY, N.Y.) In secondary cell walls (xylem and phloem tissues), the cell walls are much thicker than parenchymal cells and are linked together with lignin (Smook). This terminology is well understood in the art.

As used in the practice of the present invention, the term "dry" or "dry product" refers to a mass that contains less than 15% by weight of fibers as water.

The organic fiber mass comprises at least 50% by weight of fiber mass from organic products selected from the group consisting of sugar beets, citrus fruit, grapes, tomatoes, chicory, potatoes, pineapple, apple, carrots and cranberries. A food product or food additive may have at least 0.05 percent by weight solids in the food product or food additive of the above described highly refined cellulose product. The food product may also have at least about one percent or at least about two percent by weight of the highly refined cellulosic fiber of the invention.

A preferred method for refining cellulosic material may comprise:
soaking raw material from organic fiber plant mass comprising at least 50% by weight of all fiber mass as parenchymal fiber mass in an aqueous solution with less than 1% NaOH;
draining the raw material and allowing the raw material to sit for a sufficient period under conditions (including ambient conditions of room temperature and pressure as well as accelerated conditions) so that the fibers and cells are softened so that shearing can open up the fibers to at least 40%, at least 50%, at least 60%, or at least 70, 80, 90 or 95% of their theoretic potential. This will usually require more than 4 hours soaking to attain this range of their theoretic potential. It is preferred that this soaking is for more than 5 hours, and preferably for at least about 6 hours. This soaking time is critical to get the materials to fully soften. When such a low alkaline concentration is used in the soaking, without the set time, the materials do not completely soften and can not be sheared/opened up to their full potential. This process produces soaked raw materials; and the process continues with refining the soaked raw material to produce refined material; and drying the soaked raw material.

The process may perform drying by many different commercial methods, although some display improved performance in the practice of the present invention. It is preferred that drying is performed, at least in part, by fluid bed drying or flash drying or a combination of the two. An alternative drying process or another associated drying step is performed at least in part by tray drying. For example, fluid bed drying may be performed by adding a first stream of organic fiber plant mass and a second stream of organic fiber plant mass into the drier, the first stream having a moisture content that is at least 10% less than the moisture content of the second stream or organic fiber plant mass. The use of greater differences in moisture content (e.g., at least 15%, at least 20%, at least 25%, at least 40%, at least 50% weight-to-weight water percent or weight-to-weight water-to-solid percent) is also within the scope of practice of the invention. In the drying method, the water may be extracted with an organic solvent prior to drying. In the two stream drying process, the second stream of organic fiber plant mass may have at least 25% water to solids content and the first stream may have less than 15% water to solids content. These processes may be practiced as batch or continuous processes. The method may use chopping and washing of the cellulose mass prior to soaking.

Another description of a useful process according to the invention may include draining and washing the soaked raw material in wash water to produce washed material; bleaching the washed material in hydrogen peroxide to produce a bleached material; and washing and filtering the bleached material to produce a filtered material.

The drying of an expanded fiber material according to the invention may use room temperature or higher air temperatures that dry the expanded fiber product and maintain the fiber material's functionalities of at least two characteristics of surface area, hydrogen bonding, water holding capacity and viscosity. It is also useful to use backmixing or evaporating to bring the organic fiber plant mass to a solids/water ratio that will fluidize in air in a fluid bed air dryer. This can be particularly performed with a method that uses a fluid bed dryer or flash dryer to dry the expanded or highly refined cellulosic fiber product.

The use of a flash or fluid bed dryer is an advantage over the drying methods suggested by Dinand et al. We have found that through the use of a fluid bed or flash dryer, low temperatures and controlled humidity are not needed to dry the materials of the present invention. In fact, although nearly any drying temperature in the fluid bed or flash dryer can be used, we have dried the product of the present invention using high air temperatures (400 F) and attained a dry product with near equivalent functional properties after rehydration compared to the materials before drying. Additionally, using the process of the present invention, any surface area expanded cellulosic product can be dried and a functional product obtained and is not limited to parenchyma cell wall materials. The use of a fluid bed or flash dryer, the use of relatively high drying air temperatures (400 F+), and the ability to dry non parenchyma cell wall (secondary cell) and obtain a functional product is in great contrast to the relatively low temperatures, e.g. 100 C (212

F) and dryer types taught by Dinand et al to dry expanded parenchymal cell wall materials.

The University of Minnesota patent application (Lundberg et al), describes the ability to obtain a functional dried product. However, the only way they were able to obtain a functional dry product was through freeze drying (Gu et al, 2001).—from (Gu, L., R Ruan, P. Chen, W. Wilcke, P. Addis. 2001. *Structure Function Relationships of Highly Refined Cellulose. Transactions of the ASAE*. Vol 44(6): 1707-1712). Freeze drying is not an economically feasible drying operation for large volumes of expanded cell wall products.

The fiber products of the invention may be rehydrated or partially rehydrated so that the highly refined cellulose product is rehydrated to a level of less than 90 g $H_2O$/g fiber mass, 70 g $H_2O$/g fiber mass, 50 g $H_2O$/g fiber mass or rehydrated to a level of less than 30 g $H_2O$/g fiber mass or less than 20 g $H_2O$/g fiber mass. This rehydration process adjusts the functionalities of the product within a target range of at least one property selected from the group consisting of water holding capacity, oil holding capacity, and viscosity and may include the use of a high shear mixer to rapidly disperse organic fiber plant mass materials in a solution. Also the method may include rehydration with soaking of the dry materials in a solution with or without gentle agitation.

The HRC dispersion of the present invention is a highly viscous, semi-translucent gel. HRC embodiments comprise dried powders that are redispersable in water to form gel-like solutions. The functional characteristics of HRC are related to various properties, including water- and oil-retention capacity, average pore size, and surface area. These properties inherently relate to absorption characteristics, but the properties and benefits provided by the processes and products of the invention seem to relate to additional properties created in the practice of the invention.

The present invention also includes using an aqueous HRC gel having a lignin concentration of about one to twenty percent (1 to 20%). The HRC products of the present invention exhibit a surprisingly high WRC in the range of about 20 to at least about 56 g $H_2O$/g dry HRC. This high WRC is at least as good as, and in some cases, better than the WRC of prior art products having lower or the same lignin concentrations. The HRC products exhibit some good properties for ORC (oil retention capacity).

The resulting soaked raw material is subjected to another washing and draining. This washing and additional washing and draining tend to be more meaningful for sugar beets, potatoes, carrots (and to some degree also tomatoes, chicory, apple, pineapple, cranberries, grapes, and the like) than for citrus material. This is because sugar beets, potatoes, carrots, growing on the ground rather than being supported in bushes and trees as are citrus products, tend to pick up more materials from the soil in which they grow. Sugar beets and carrots tend to have more persistent coloring materials (dyes, pigments, minerals, oxalates, etc.) and retained flavor that also are often desired to be removed depending upon their ultimate use. In one embodiment, the soaked raw material is washed with tap water. In one other embodiment, the material is drained. This is optionally followed by bleaching the material with hydrogen peroxide at concentrations of about one (1) to 20% (dry basis) peroxide. The bleaching step is not functionally necessary to effect the citrus and grape fiber conversion to highly refined cellulose. With respect to carrots and sugar beets, some chemical processing may be desirable, although this processing may be significantly less stressful on the fiber than the bleaching used on corn-based HRC products. From our experience, some chemical step is required for sugar beets, and bleaching is one option. Using alkaline pretreatment baths is another option. Acid treatment or another bleaching agent are other options.

The material is optionally bleached at about 20 to 100° C. for about five (5) to 200 min. The bleached material is then subjected to washing with water, followed by filtering with a screen. The screen can be any suitable size. In one embodiment, the screen has a mesh size of about 30 to 200 microns.

The filtered material containing solids can then be refined (e.g., in a plate refiner, stone mill, hammer mill, ball mill, or extruder.). In one embodiment, the filtered material entering the refiner (e.g., a plate refiner) contains about four percent (4%) solids. In another embodiment, the refining can take place in the absence of water being added. The plate refiner effectively shreds the particles to create microfibers. The plate refiner, which is also called a disk mill, comprises a main body with two ridged steel plates for grinding materials. One plate, a refining plate, is rotated while a second plate remains stationary. The plates define grooves that aid in grinding. One plate refiner is manufactured by Sprout Waldron of Muncy, Pa. and is Model 12-ICP. This plate refiner has a 60 horsepower motor that operates at 1775 rpm.

Water may be fed into the refiner to assist in keeping the solids flowing without plugging. Water assists in preventing the refiner's plates from overheating, which causes materials in the refiner to burn. (This is a concern regardless of the type of grinding or shearing device used.). The distance between the plates is adjustable on the refiner. To set refining plate distances, a numbered dial was affixed to the refining plate adjustment handle. The distance between the plates was measured with a micrometer, and the corresponding number on the dial was recorded. Several plate distances were evaluated and the setting number was recorded. A variety of flow consistencies were used in the refiner, which was adjusted by varying solids feed rate. The amount of water flowing through the refiner remained constant. Samples were sent through the refiner multiple times. In one embodiment the materials are passed one or more times through the plate refiner.

The microfibers may then be separated with a centrifuge to produce refined materials. The refined materials are then diluted in water until the solids content is about 0.5 to 37%. This material is then dispersed. In one embodiment, dispersing continues until a substantially uniform suspension is obtained, about 2 to 10 minutes. The uniform suspension reduces the likelihood of plugging.

The resulting dispersed refined materials, i.e., microparticles, may then be homogenized in any known high pressure homogenizer operating at a suitable pressure. In one embodiment, pressures greater than about 5,000 psi are used. The resulting highly refined cellulose (HRC) gel may display a lignin content of about 1 to 20% by weight, depending in part upon its original content.

The absence of use of a mild NaOH soaking before the refining step in the present invention prior to high pressure homogenization does not require the use of high temperature and high pressure cooking (high temperature means a temperature above 100 degrees C. and high pressure means a pressure above 14 psi absolute). High temperature and high pressure cooking may be used, but to the disadvantage of both economics and output of the product. This novel process further avoids the need for either mild concentrations of NaOH or of highly concentrated NaOH and the associated undesirable environmental impact of discharging waste water containing any amount of NaOH and organic compounds. The process also avoids a need for an extensive recovery system. In one embodiment, the pH of the discharge stream in the present invention is only about 8 to 9 and may even approach 7. The method of the present invention has the further advantage of reducing water usage significantly over prior art processes, using only about one third to one-half the amount of water as is used in conventional processes to produce to produce HRC gel and amounts even less than that used in the Chen processes All of the mechanical operations, refining, centrifuging, dispersing, and homogenizing could be viewed as optional, especially in the case of citrus pulp or other tree bearing fruit pulps. Additionally, other shearing operations can be used, such as an extruder, stone mill, ball mill, hammer mill, etc. For citrus pulp, the only processes that are needed to produce the expanded cell structure are to dry (using the novel drying process) and then properly hydrate the raw material prior to the expanding and shearing step of the process of the invention. This simple process could also be used in other raw material sources.

Hydration is a term that means reconstituting the dried fiber back to a hydrated state so that it has functionality similar to the pre-dried material. Hydration can be obtained using various means. For instance, hydration can occur instantly by placing the dry products in a solution followed by shearing the mixture. Examples of shearing devices are a high shear disperser, homogenizer, blender, ball mill, extruder, or stone mill. Another means to hydrate the dry materials is to put the dry product in a solution and mix the materials for a period of time using gentle or minimal agitation. Hydrating dry materials prior to use in a recipe can also be conducted on other insoluble fibrous materials to enhance their functionality.

The initial slurry of fibers/cells from the EPM products is difficult to dry. There is even disclosure in the art (e.g., U.S. Pat. Nos. 4,413,017 and 4,232,049) that slurries of such processed products cannot be easily dried without expensive and time consuming processes (such as freeze drying, extended flat bed drying, and the like). Freeze drying is effective, but is not economically and/or commercially desirable. Similarly, tray dryers may be used, but the length of time, labor and energy requirements make the process costly. The slurries of the citrus and/or beet by-products may be dried economically and effectively according to the following practices of the invention. Any type of convective drying method can be used, including a flash dryer, fluid bed dryer, spray dryer, etc. One example of a dryer that can be used is a fluid bed dryer, with dry material being added to the slurry to equilibrate the moisture content in the materials. It has been found that by adding 5:1 to 1:1 dry to wet materials within the fluid bed drier improves the air flow within the drier and the material may be effectively dried. In the absence of the combination of "dry" and "wet" materials, the slurry will tend to merely allow air to bubble through the mass, without effective drying and without a true fluid bed flow in the drier. The terms wet and dry are, of course, somewhat relative, but can be generally regarded as wet having at least (>40% water/<60% solid content] and dry material having less than 20% water/80% solid content). The amounts are not as critical as the impact that the proportional amounts of materials and their respective water contents have in enabling fluid flow within the fluid bed drier. These ranges are estimates. It is always possible to use "wet" material with lower moisture content, but that would have to have been obtained by an earlier drying or other water removal process. For purpose of economy, and not for enabling manufacture of HRC microfibers according to the present invention from citrus or beet by-product, it is more economical to use higher moisture content fiber mass as the wet material. After the mixture of wet and dry materials have been fluid bed dried (which can be done with air at a more moderate temperature than is needed with flat bed dryers (e.g., room temperature air with low RH may be used, as well as might heated air). A flash drier may also be used alternatively or in combination with a fluid bed drier to effect moisture reduction from the citrus or beet by-product prior to produce a functional dry product. It would be necessary, of course, to control the dwell time in the flash drier to effect the appropriate amount of moisture reduction and prevent burning. These steps may be provided by the primary or source manufacturer, or the product may be provided to an intermediate consumer who will perform this drying step to the specification of the process that is intended at that stage.

One aspect of the drying process is useful for the drying of any expanded cellulose products, especially for the drying of highly refined cellulose fibers and particles that have been extremely difficult or expensive to dry. Those products have been successfully dried primarily only with freeze drying as a commercially viable process. That process is expensive and energy intense. A method according to the present invention for the drying of any expanded cellulose fiber or particle product comprises drying an expanded cellulose product by providing a first mass of expanded cellulose fiber product having a first moisture content as a weight of water per weight of fiber solids; providing a second mass of expanded cellulose fiber product having a second moisture content as a weight of water per weight of fiber solids, the second moisture content being at least 20% less than said first moisture content; combining said first mass of expanded cellulose fiber product and said second mass of expanded cellulose product to form a combined mass; drying said combined mass in a drying environment to form a dried combined mass. The method may have the dried combined mass dried to a moisture content of less than 20, less than 10, less than 8, less than 5 or less than 3 $H_2O/g$ fiber mass. The method, by way of non-limiting examples, may use drying environments selected from the group consisting of, flash driers, fluid bed driers and combinations thereof.

The rehydration and shearing (particularly high shearing at levels of at least 10,000 $sec^{-1}$, preferably at least 15,000 $sec^{-1}$, more often, greater than 20,000, greater than 30,000, greater than 40,000, and conveniently more than 50,000 $sec^{-1}$ (which is the actual shearing rate used in some of the examples) of the dry fiber product enables the resultant sheared fiber to retain more moisture and to retain moisture more strongly. It has been noted in the use of materials according to the practice of the invention that when the fiber products of the invention are rehydrated, the water activity level of rehydrated fiber is reduced in the fiber (and the fiber present in a further composition) as compared to free water that would be added to the further composition, such as a food product. The food products that result from cooking with 0.1 to 50% by weight of the HRC fiber product of the invention present has been found to be highly acceptable to sensory (crust character, flavor/aroma, grain/texture, taste, odor, and freshness, especially for mixes, frozen foods, baked products, meat products and most particularly for bakery goods, bakery products, and meat products) tests on the products. Importantly, the products maintain their taste and mouth feel qualities longer because of the higher moisture retention.

Viscosity Measuring Procedure

Measure the viscosity using a Brookfield DV II+ viscometer using cylindrical spindles at 10 rpm with a 3% by weight solids/water solution at room temperature (25° C.±3° C.) for 1 minute.

Any suitable amount of plant mass, fiber material (in particle or fiber or fibrid form) or highly refined cellulose effective to increase viscosity in the aqueous liquid may be used. In a preferred embodiment, the highly refined cellulose component is present in the aqueous liquid an amount sufficient to provide greater than or equal to about 0.005% w/w highly refined cellulose, more preferably from greater than about 0.1% w/w, and still more preferably from about 0.2% w/w to about 1% w/w highly refined cellulose concentration in the product. Unless otherwise specified, the concentrations of highly refined cellulose given herein are based on the weight of non-hydrated highly refined cellulose. No matter which process is used, any amount of highly refined cellulose effective to provide a measurable increase in viscosity (based on about 100% w/w of the liquid composition to which the enzymatically modified refined cellulose is added) from about 1% w/w to about 30% w/w composition, from about 30% w/w to about 80% w/w water, up to about 50% w/w composition, and from about 0.005% w/w to about 3.0% w/w highly refined cellulose, should be used.

Suitable aqueous plant mass, fiber or highly refined cellulose compositions are made by blending the components of the solution in water. In one embodiment, the plant mass, fiber or aqueous highly refined cellulose composition consists essentially of highly refined cellulose in water. As used herein, the term "water" generally refers to tap water, that is, water as available onsite without requiring purification that may contain minor amounts of components other than H2O. However, any suitable water may be used.

The aqueous highly refined cellulose composition may, optionally, further comprise other components, such as for example, alkali metal silicates, alkali metal salts, such as for example, NaCl, KCl, and surfactants suitable for food use and other viscosity modifiers.

Also, in a preferred embodiment, the aqueous highly refined cellulose composition is at a temperature of from about 0 to about 85 C, more preferably from 0 to about 70 C, still more preferably from about 0 C to about 50 C., and even more preferably from about 0 C to about 20 C.

It should also be appreciated that the compositions of the solutions and methods used in the process of the invention may be varied according to the desired characteristics of the food product. The following non-limiting examples will further illustrate the preparation and performance of the invention. However, it is to be understood that these examples are given by way of illustration only and are not a limitation of the invention.

What is claimed:

1. A mixture consisting essentially of active probiotic agents stabilized by at least 1% by weight of highly refined cellulose fiber material with respect to the probiotic agents.

2. The mixture of claim 1 wherein the highly refined cellulose fiber material has been dry-blended with the probiotic agents to form a mixture having at least 2% by weight and up to 98% by weight of the highly refined cellulose fiber with respect to the total weight of the highly refined cellulose fiber and the probiotic.

3. The mixture of claim 2 wherein the highly refined cellulose fiber material further comprises a high parenchymal content fiber reagent that has organic fiber plant mass comprising at least 30% by weight of all fiber mass as parenchymal fiber mass and a hydrocolloid bound to the fiber during shearing of an unrefined cellulose fiber mass during formation of a highly refined cellulose mass as a high parenchymal fiber additive product having at least 10% by total weight of insoluble fiber.

4. The mixture of claim 2 wherein the highly refined cellulose comprises chicory root.

5. The mixture of claim 2 consisting of active probiotic agents stabilized by at least 2% by weight of highly refined cellulose fiber material with respect to the probiotic agents.

6. The mixture of claim 1 in a dried powder state.

7. The mixture of claim 1 wherein the highly refined cellulose comprises chicory root.

8. The mixture of claim 1 consisting of active probiotic agents stabilized by at least 1% by weight of highly refined cellulose fiber material with respect to the probiotic agents.

9. A mixture consisting essentially of active probiotic agents stabilized by at least 1% by weight of highly refined cellulose fiber material with respect to the probiotic agents and a liquid, the mixture and liquid flowing as a liquid at 20 C and 760 mm Hg atmospheric pressure and 40% relative humidity.

10. The mixture of claim 9 as a frozen mass.

11. A method for moderating dysphagia comprising: identifying a patient with dysphagia, administering the mixture of claim 9 as a thickened liquid, viscosity of the-liquid mixture being sufficient to assist in moderating swallowing difficulties by the patient.

12. The mixture of claim 9 wherein the highly refined cellulose fiber material further comprises a high parenchymal content fiber reagent that has organic fiber plant mass comprising at least 30% by weight of all fiber mass as parenchymal fiber mass and a hydrocolloid bound to the fiber during shearing of an unrefined cellulose fiber mass during formation of a highly refined cellulose mass as a high parenchymal fiber additive product having at least 10% by total weight of insoluble fiber.

13. The mixture of claim 9 consisting of active probiotic agents stabilized by at least 1% by weight of highly refined cellulose fiber material with respect to the probiotic agents.

14. A mixture consisting essentially of active probiotic agents stabilized by at least 1% by weight of highly refined cellulose fiber material with respect to the probiotic agents and wherein the highly refined cellulose fiber material is a high parenchymal content fiber reagent that has organic fiber plant mass comprising at least 30% by weight of all fiber mass as parenchymal fiber mass and a hydrocolloid bound to the fiber during shearing of an unrefined cellulose fiber mass during formation of a highly refined cellulose mass as a high parenchymal fiber additive product having at least 10% by total weight of insoluble fiber.

15. The mixture of claim 14 wherein the highly refined cellulose comprises chicory root.

* * * * *